United States Patent [19]

Khanna

[11] Patent Number: 4,798,724
[45] Date of Patent: Jan. 17, 1989

[54] SOLID, STABLE DOSAGE FORMS WITH AN ELASTIC FILM COATING

[75] Inventor: Satish C. Khanna, Bottmingen, Switzerland

[73] Assignee: Ciba-Geigy Corporation, Ardsley, N.Y.

[21] Appl. No.: 874,772

[22] Filed: Jun. 16, 1986

[30] Foreign Application Priority Data

Jun. 24, 1985 [CH] Switzerland .................. 2664/85

[51] Int. Cl.$^4$ .................. A01N 25/10; A61K 31/78
[52] U.S. Cl. .................. 424/480; 424/81
[58] Field of Search .................. 424/33, 35, 461, 480, 424/494, 81

[56] References Cited

U.S. PATENT DOCUMENTS

| | | | |
|---|---|---|---|
| 4,308,251 | 12/1981 | Dunn et al. .................. | 424/19 |
| 4,361,546 | 11/1982 | Stricker et al. .................. | 424/480 |
| 4,389,393 | 6/1983 | Schor et al. .................. | 424/35 |
| 4,486,471 | 12/1984 | Samejima et al. .................. | 424/33 |
| 4,490,322 | 12/1984 | Zierenberg .................. | 424/81 |
| 4,606,909 | 8/1986 | Bechgaard et al. .................. | 424/480 |

FOREIGN PATENT DOCUMENTS

| | | | |
|---|---|---|---|
| 44-9294 | 4/1969 | Japan .................. | 424/480 |
| 8110943 | 6/1983 | Japan .................. | 424/480 |

*Primary Examiner*—Joseph L. Schofer
*Assistant Examiner*—Peter F. Kulkosky
*Attorney, Agent, or Firm*—Irving M. Fishman

[57] ABSTRACT

Solid, stable dosage forms consisting of a moisture- and temperature-sensitive core prepared from a medicament, or a mixture of medicaments, and excipients, and an elastic film coating which decomposes in aqueous solution, said elastic film coating substantially comprising (a) a water-soluble component consisting of
  20–60% of hydroxypropyl cellulose having an average molecular weight of 75,000, and
(b) a water-insoluble component consisting of
  5–20% of an acrylic resin in the form of
    ($b_1$) a 70:30 ethyl acrylate/methyl methacrylate copolymer having a molecular weight of 80,000, or
    ($b_2$) a 30:70 to 70:30 methyl acrylate/methyl methacrylate copolymer having an average molecular weight of 500,000,
  20–60% of a lubricant,
  0.5–5% of a wetting agent,
  0–5% of a plasticizer,
and optional additional excipients, and process for the preparation thereof.

8 Claims, No Drawings

SOLID, STABLE DOSAGE FORMS WITH AN ELASTIC FILM COATING

The present invention relates to solid, stable dosage forms provided with an elastic film coating.

Because of their composition, solid dosage forms such as tablets, film-coated dragées or pellets have a tendency to undergo unsightly changes in shape, e.g. swelling, shrinkage or cracking, under the influence of high humidity and/or increased ambient temperature, These changes may be off-putting to the consumer and/or patient and provoke a negative reaction. To prevent such a reaction, attempts have been made to provide such dosage forms with film coatings of a certain elasticity, especially with polymeric coating materials. Many coatings are known and commercially available, but these are not elastic (q.v. U.S. Pat. No. 4,140,756).

Surprisingly, it has now been found that it is possible to prepare a particularly elastic, stable coating which decomposes in aqueous solution with a very specific mixture of hydroxypropyl cellulose and one of two specific acrylic resins, in a specific mixture ratio, which coating is also able to withstand intact appreciable changes in the solid core coated therewith.

The solid, stable dosage form of this invention is characterised in that it consists of a moisture- and/or temperature-sensitive core prepared from medicament, or a mixture of medicaments, and excipients, and an elastic film coating which decomposes in aqueous solution, said elastic film coating substantially comprising (a) a water-soluble component consisting of
   20–60% of hydroxypropyl cellulose having an average molecular weight of 75,000, and
(b) a water-insoluble, but dispersible, component consisting of
   5–20% of an acrylic resin in the form of
   ($b_1$) a 70:30 ethyl acrylate/methyl methacrylate copolymer having a molecular weight of 80,000, or
   ($b_2$) a 30:70 to 70:30 methyl acrylate/methyl methacrylate copolymer having an average molecular weight of 500,000,
   20–60% of a lubricant,
   0.5–5% of a wetting agent,
   0–5% of a plasticiser, and optional additional excipients. The percentages are in each case percentages by weight.

A preferred solid dosage form is one provided with an elastic film coating which decomposes in aqueous solution and which comprises 30–50% of hydroxypropyl cellulose, 8–18% of an acrylic resin, 30–50% of a lubricant, 1–2% of a wetting agent, and 0–3% of a plasticiser.

Suitable solid dosage forms consisting of medicament and excipients are the compressed tablets and pellets customarily employed in pharmaceutics and prepared by known methods. Examples of medicaments which can induce changes in shape under the influence of humidity and/or temperature are: potassium chloride, e.g. in the form of tablets according to European patent application EP-B1-No. 0 052 076, or diclofenac in the form of resinate tablets according to European patent application EP-A No. 2-0 122 219.

Excipients for incorporation in the solid dosage forms are e.g. ion exchangers of cationic or anionic character, e.g. crosslinked polyvinylpolypyrrolidone, starch, e.g. corn starch, or crosslinked starches USP, crosslinked carboxymethyl cellulose USP, polyacrylic acid, crosslinked polyethylene glycols, natural rubbers such as tragacanth and alginates. Further suitable medicaments are in particular those which may cause gastric disorders in patients with sensitive stomachs, e.g. pirprofen.

The hydroxypropyl cellulose used for the elastic film coating is suitably hydroxypropyl cellulose having an average molecular weight of 75,000, in particular Klucel®L, sold by Hercules Inc., Wilmington, Del. (USA).

The preferred acrylic resin is ($b_1$) the 70:30 ethyl acrylate/methyl methacrylate copolymer sold under the registered trademark Eudragit®E30D (as 30% aqueous dispersion) by Röhm Pharma GmbH, Darmstadt (Federal Republic of Germany);

($b_2$) the 30:70 to 70:30 methyl acrylate/methyl methacrylate copolymer sold under the registered trademark Mamma-Resin®100 (as 31% aqueous dispersion) by Rohm and Haas, Milan, Italy.

The lubricant may be for example magnesium stearate, silica aerogel and, preferably, talcum.

Suitable wetting agents are glyceryl polyethylene glycol oxystearate (e.g. Cremophor®RH 40) or polyoxyethylene sorbitan fatty acid ester (e.g. Tween®80)

If the methyl acrylate/methyl methacrylate copolymer is used as the acrylic resin, then it is also necessary to use a plasticiser. A particularly suitable plasticiser is Triacetin® (glycerol triacetate).

Optional ingredients of the film coating comprise pigments such as coloured iron oxides, or titanium dioxide, and/or flavourings such as sweeteners (e.g. saccharine, sodium cyclamate or sugar).

Any process and/or machine suitable for an enteric film-coating process may be employed for preparing the dosage forms of this invention, i.e. preferably coating drums and fluidised bed coaters.

The dosage forms so obtained provided with an elastic film coating have the property that the film coating dissolves rapidly in the patient's stomach, so that the released core is able to act immediately in accordance with its intended purpose.

EXAMPLE 1

| Composition (according to EP-B1 0 052 075) | Per tablet | Per batch |
|---|---|---|
| A. Cores | | |
| potassium chloride | 600 mg | 6000 g |
| Eudragit ® E30D (solid) | 140 mg | 1400 g |
| Aquacoat ® ECD (ethyl cellulose solid) | 44 mg | 440 g |
| talcum | 12 mg | 120 g |
| Aerosil ® 200 (silica) | 2 mg | 20 g |
| Avicel ® PH 101 (microcrystalline cellulose) | 68 mg | 680 g |
| Polyplasdone ® XL (polyvinylpolypyrrolidone) | 50 mg | 500 g |
| magnesium stearate | 4 mg | 40 g |
| | 920 mg | 9200 g |
| B. Film coating | | |
| Klucel ® L | 14.8 mg | 148 g |
| Eudragit ® E 30D (solid) | 4.9 mg | 49 g |
| Cremophor ® RH 40 | 5.0 mg | 5 g |
| talcum | 8.8 mg | 88 g |
| titanium dioxide | 1.5 mg | 15 g |
| | 30.5 mg | 305 g |
| Total | 950.5 mg | 9505 g |

Preparation

A. Cores

Potassiuum chloride crystals are sprayed with a mixture of Eudragit ®E 30D (dispersion) in a fluidised bed granulator (Aeromatik) at an air temperature of 28° C. After the crystals have been sprayed with the total amount of dispersion mixture, the coated KCl crystals are dried for 10 minutes in a fluidised bed drier at an air temperature of 28° C. Talcum is mixed with the dried, coated KCl crystals for 10 minutes and the mixture is passed through a sieve having a mesh size of 1.5–2 mm in order to remove any agglomerates. Avicel ®PH 101, Polyplasdone ®XL, Aerosil ®200 and magnesium stearate are added and the ingredients are mixed for 10 minutes. The mixture is compressed in a commercially available tabletting machine (Kilian Pharma I) to rod-shaped tablets measuring 17.4×8.6 mm.

B. Film-coating

1. Klucel ®L and Cremophor ®RH 40 are dissolved in 1.2 kg of demineralised water. The talcum is added, with stirring, and then suspended for about 45 minutes until a homogeneous dispersion is obtained. Finally, Eudragit ®E 30D is stirred in.

2. The cores are put into a perforated coating drum (Accela-Cota, 24 inches) and coated under the following test conditions:

| | |
|---|---|
| air flow | 300 m³/h |
| spent air | 500 m³/h |
| air temperature | 35°–50° C. |
| drum rotation speed | 12 rpm |
| pump | elastic tube pump |
| jet | 1–7 |
| ventilator | 170 G |
| spraying pressure | 2 bar |
| temperature of cores | 25°–40° C. |

Stability Test:

The volume of the tablets stored under humid conditions (30° C., 80% rel. humidity, 1 week) increases by up to 30%. The film coating proves elastic and exhibits no cracking or chipping.

EXAMPLE 2

| Composition | |
|---|---|
| A. Cores (for 1000 tablets) (according to EP-A2 0 122 219) | |
| diclofenac sodium | 100 g |
| cholestyramine USP | 200 g |
| Avicel ® PH 101 | 37 g |
| Aerosil ® 200 | 3.4 g |
| magnesium stearate | 2.6 g |
| | 343.0 g |
| B. Film coating (for 1000 tablets) | |
| methyl acrylate/methyl methacrylate copolymer (solid) | 5.5 g |
| Triacetin ® | 0.7 g |
| Klucel ® L | 5.7 g |
| Cremophor ® RH 40 | 0.6 g |
| talcum | 11.0 g |

Preparation

A. Cores 100 g of diclofenac sodium are dissolved in 5 liters of deionised water and then 200 g of cholestyramine (granular size: 80 μm) are slowly dispersed in this solution. The mixture is stirred for about 12 hours at 50° C. The resinate of the medicament that forms is isolated by filtration and dried to constant weight at 50° C. in vacuo.

The other solid ingredients are first passed through a 0.6 mm sieve and then mixed for about 10 minutes. This mixture is compressed to cores which are domed on both sides in an eccentric tabletting machine (Kilian EKO). The cores weigh about 343 mg and have a diameter of 10 mm. Each tablet contains medicament corresponding to 100 mg of diclofenac sodium.

B. Film coating (1) Klucel ®L and Cremophor ®RH 40 are dissolved in 110 g of demineralised water. The talcum is stirred in and mixed for about 15 minutes until a homogeneous dispersion is obtained. Finally, the methyl acrylate/methyl methacrylate (as 30% dispersion) and Triacetin ® are stirred in.

(2) The cores are sprayed with the coating dispersion in a fluidised bed coater (Aeromatic Strea 1) at an air temperature of 20° C. After the total amount of coating dispersion has been sprayed onto the cores, the coated cores are dried for about 10 minutes in a fluidised bed drier at an air temperature of 30° C.

Stability test
as in Example 1.

What is claimed is:

1. A solid, stable dosage form consisting of a core and an elastic film coating on said core, said core comprising at least one medicament and at least one pharmaceutically acceptable excipient, said core being moisture- or temperature- or both moisture- and temperature-sensitive; said elastic film coating being a coating which decomposes in aqueous solution, which coating comprises
   (a) 20–60% by weight of a water soluble component,
   (b) 25.5–80% by weight of a water-insoluble, but dispersable component, and
   (c) 0.54–5% by weight of further pharmaceutically acceptable adjuvants,
said water soluble component consisting of hydroxypropyl cellulose having an average molecular weight of 75,000; said water-insoluble, but dispersable component consisting of
   (I) 5–20% by weight, based upon the total film coating, of an acrylic resin selected from
      (A) a 70:30 ethyl acrylate/methyl methacrylate copolymer having a molecular weight of 80,000 and
      (B) a 30:70–70:30 methyl acrylate/methyl methacrylate copolymer having an average molecular weight of 500,000;
   (II) 20–60% by weight, based on the total film coating, of a pharmaceutically acceptable lubricant;
   (III) 0.5–5% by weight, based on the total film coating, of a pharmaceutically acceptable wetting agent; and
   (IV) 0–5% by weight, based on the total film coating, of a pharmaceutically acceptable plasticiser.

2. The dosage form of claim 1 wherein said film coating comprises
   30–50% by weight of said hydroxypropyl cellulose;
   8–18% by weight of said acrylic resin;
   30–50% by weight of said lubricant;
   1–2% by weight of said wetting agent; and
   0–3% by weight of said plasticiser.

3. The dosage form of claim 1 wherein said lubricant is selected from magnesium stearate, silica aerogel, and talcum.

4. The dosage form of claim 1 wherein said wetting agent is selected from glycerylpolyethylene glycol oxystearates and polyoxyethylene sorbitan fatty acid esters.

5. The dosage form of claim 1 wherein said plasticiser is glycerol triacetate.

6. The dosage form of claim 1 wherein said further adjuvants are selected from pigments flavorings, and sweeteners.

7. The dosage form of claim 1 wherein said excipient is pharmaceutically acceptable and selected from ion exchangers, starch, crosslinked starches, crosslinked carboxymethylcellulose, polyacrylic acid, crosslinked polyethylene glycols, natural rubbers, and alginates.

8. A process for the manufacture of the dosage form of claim 1 comprising coating said core with said elastic film coating.

* * * * *